United States Patent [19]

Chapman

[11] 4,286,110
[45] Aug. 25, 1981

[54] SEPARATION OF PRODUCTS OF HF ALKYLATION

[75] Inventor: Charles C. Chapman, Bartlesville, Okla.

[73] Assignee: Phillips Petroleum Co., Bartlesville, Okla.

[21] Appl. No.: 112,886

[22] Filed: Jan. 17, 1980

[51] Int. Cl.³ .............................................. C07C 2/56
[52] U.S. Cl. ................................... 585/719; 585/723
[58] Field of Search ................................ 585/719, 723

[56] References Cited

U.S. PATENT DOCUMENTS

| 2,910,521 | 10/1959 | Cobb | 585/701 |
|---|---|---|---|
| 3,000,991 | 9/1961 | Goldsby et al. | 585/311 |
| 3,007,982 | 11/1961 | Clauson | 585/715 |
| 3,007,983 | 11/1961 | Clauson | 585/715 |
| 3,204,011 | 8/1965 | Hettick et al. | 585/703 |
| 3,370,003 | 2/1968 | Borst | 585/719 |
| 3,763,022 | 10/1973 | Chapman | 585/717 |
| 3,855,344 | 12/1974 | Jones | 585/716 |
| 3,857,904 | 12/1974 | Chapman | 585/719 |
| 3,929,924 | 12/1975 | Chapman | 585/703 |
| 3,957,901 | 5/1976 | Chapman | 585/701 |
| 4,112,010 | 9/1978 | Dixon | 585/723 |
| 4,180,526 | 12/1979 | Chapman | 585/719 |
| 4,182,925 | 1/1980 | Chapman | 585/719 |

Primary Examiner—Curtis R. Davis

[57] ABSTRACT

The reactor effluent hydrocarbon phase from an alkylation zone in which isoparaffin and olefin are contacted in the presence of HF catalyst to form an alkylate product is treated by (1) separating a hydrocarbon phase from the reacton effluent; (2) separating the hydrocarbon phase in a fractionator to produce a bottoms stream containing isoparaffin, paraffin, and alkylate and an overhead stream containing HF, isoparaffin, and paraffin; (3) flashing this bottoms stream to produce a flashed vapor enriched in isoparaffin and a liquid enriched in alkylate as compared to the bottoms stream; (4) cooling this flashed vapor to produce a condensed liquid; and (5) indirectly contacting this condensed liquid with the overhead stream thereby cooling the overhead stream and heating the condensed liquid. In further embodiments of the invention flashing the condensed liquid thereby producing (a) a flashed vapor further enriched in paraffin which is then compressed and further treated to remove residual isoparaffin and (b) a liquid further enriched in isoparaffin which is recycled to the alkylation zone. In another embodiment of the invention the overhead stream is condensed by contact with the condensed liquid, pumped into contact with HF thereby removing organic fluorides, and is then subjected to treatment effecting separation of paraffin from isoparaffin.

6 Claims, 1 Drawing Figure

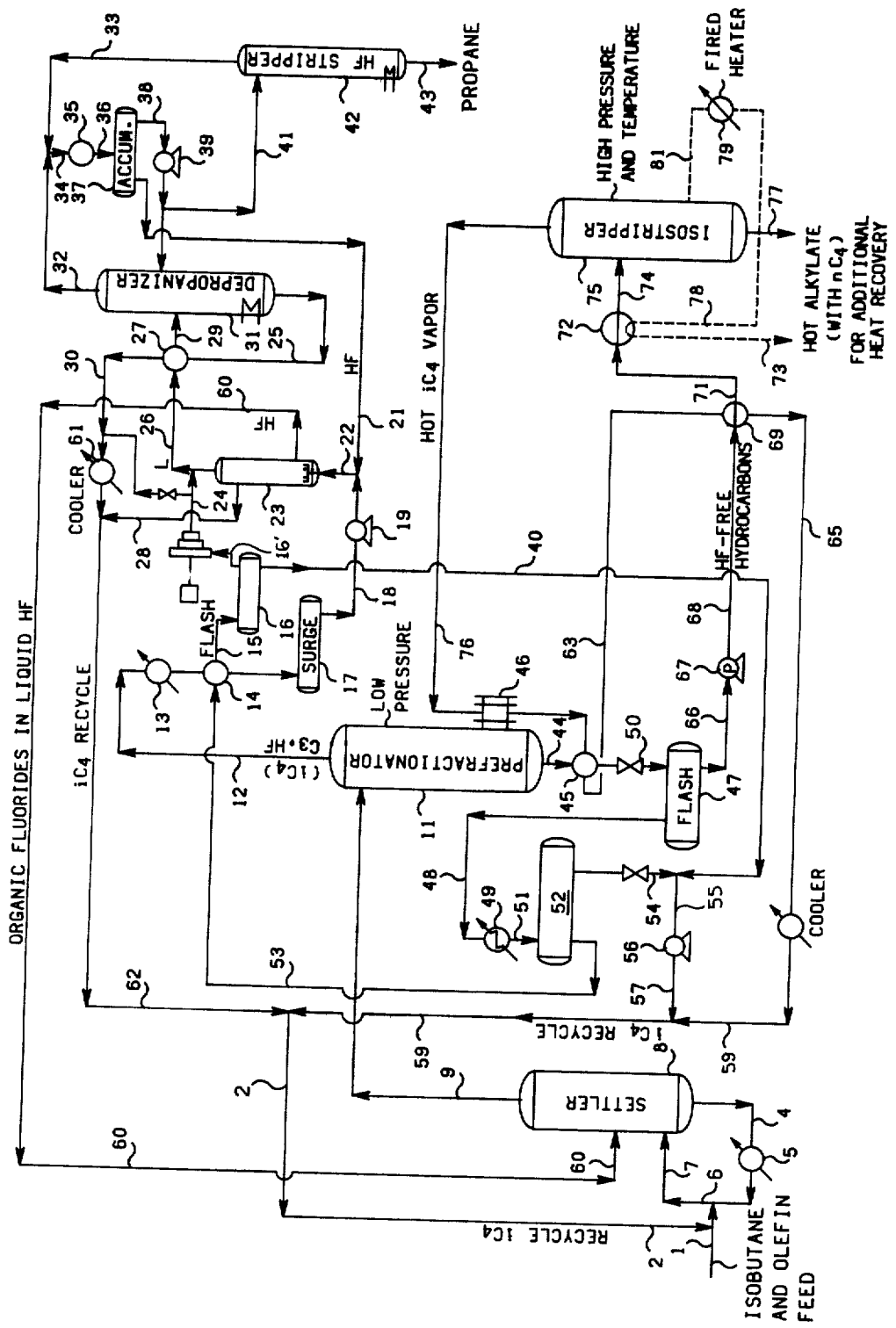

SEPARATION OF PRODUCTS OF HF ALKYLATION

BACKGROUND OF THE INVENTION

This invention relates to the reaction and recovery of products in a hydrogen fluoride (HF) catalyzed alkylation. In one of its aspects, this invention relates to the contact of isoparaffin with olefin in the presence of HF catalyst to produce alkylate product. In another of its aspects, this invention relates to the supplying of energy for the separation of the reaction products of an alkylation process.

Various schemes have been proposed to maximize the efficiency of energy use in the separation of the components of the effluent from various chemical reactions. Some reactions, such as the contact of isoparaffin with olefin in the presence of an HF catalyst to produce an alkylate product, produce an effluent that contains a variety of components that can be profitably separated as salable product or for recycle into the reaction process. Since the reaction effluent also contains impurities that can be harmful to the salability of the product or to the efficiency of the reaction, the removal of these impurities also becomes an important factor to consider in the treatment of the reaction effluent. Effluent treatment is, therefore, a multi-faceted problem that lends itself to a variety of solutions.

In the present invention use is made of multiple flashing, condensing, and indirect contact of the bottoms stream and overhead stream from the fractionation of the reactor effluent hydrocarbon phase from an alkylation zone to effect economies of energy use in the process.

It is therefore an object of this invention to provide a method for separating isoparaffin from the hydrocarbon phase in an alkylation reactor effluent which results in economies both in equipment and energy usage. It is another object of the invention to provide a system for flashing, condensing, and indirectly contacting material from the bottoms and overhead streams from a fractionator to effect economies in the process. It is still another object of this invention to provide a method for treating the overhead stream from a fractionator containing paraffin, HF, isoparaffin, and organic fluoride impurities so that the organic impurities are removed.

Other aspects, objects, and the various advantages of this invention will become apparent upon reading this specification and the appended claims.

STATEMENT OF THE INVENTION

According to this invention a process is provided for treating the reactor effluent hydrocarbon phase from an alkylation zone in which isoparaffin and olefin are contacted in the presence of HF catalyst to form alkylate product. In the process (1) a hydrocarbon phase is separated from the reaction effluent; (2) the hydrocarbon phase is then separated in a fractionator to produce a bottoms stream containing isoparaffin, paraffin, and alkylate product and to produce an overhead stream containing paraffin, HF, isoparaffin, and organic fluoride impurities; (3) the bottoms stream is flashed to produce a flashed vapor enriched in isoparaffin and a liquid enriched in alkylate as compared to the bottoms streams; (4) the flashed vapor stream is cooled to produce a condensed liquid; and (5) the condensed liquid is indirectly contacted with the overhead stream from the fractionator thereby cooling the overhead stream and heating the condensed liquid.

In further embodiments of the invention the indirect contact of the condensed liquid with the overhead stream flashes the condensed liquid to produce a flashed vapor further enriched in paraffin and a liquid further enriched in isoparaffin. This flashed vapor further enriched in paraffin is then compressed and further treated to remove the residual isoparaffin. The liquid is recycled to the alkylation zone.

In another embodiment of the invention the indirect contact of the condensed liquid and the overhead stream condenses the overhead stream which is then pumped to contact a sufficient amount of HF to remove organic fluoride impurities with this treated overhead stream then being subjected to further treatment effecting separation of paraffin from isoparaffin.

The invention can best be understood in conjunction with the drawing which is a schematic representation of the process according to this invention.

Referring now to the drawing, fresh olefin and isoparaffin, which for the sake of this illustration are butylene and isobutane, respectively, are charged through line 1 along with recycle isobutane from line 2 into an alkylation zone 6 along with HF catalyst. Reaction conditions well known in the art are maintained in the reactor so that an alkylate product is produced. Effluent from the reactor flows through line 7 into a liquid full settler 8 in which hydrogen fluoride settles and is circulated through line 4 and cooler 5 into fresh contact with the olefin and isoparaffin feedstock.

A hydrocarbon phase containing alkylate, isobutylene, propane, HF, and organic fluoride impurities is pressured through line 9 to a first fractionator 11 which can be denominated a low pressure prefractionator. From this fractionator is produced an overhead stream containing isobutane, propane, HF, and organic fluoride impurities and a bottoms stream containing predominantly isobutane and alkylate with some propane.

The bottoms stream 44 containing isobutane and alkylate is passed from low pressure prefractionator 11 through a pressure regulator 50 into flash tank 47 where flashed vapor enriched in isobutane and a flashed liquid enriched in alkylate, as compared to the flash tank feed, is produced. Preferably the bottoms stream 44 is passed through heat exchanger 45 before being flashed so that the flashed vapor is even more enriched with isobutane and flashed liquid is even more enriched with alkylate. The flashed vapor is passed through line 48 to indirect contact cooler 49 where it is condensed, through line 51 and into surge tank 52. The condensed liquid is then passed through line 53 to cooler 14 for indirect contact with the overhead from prefractionator 11 which is passed through line 12 and precooler 13 before contact with the condensed liquid. It is an object of the invention that the contact between the two streams in heat exchanger 14 be sufficient to condense the overhead stream which is then passed to surge tank 17 and to cause flashing of the condensed liquid which is then passed through line 15 into surge tank 16.

The liquid from surge tank 16 is transferred through lines 40 and 55, optionally to be joined by liquid passing from tank 52 through line 54, to the suction of pump 56 to be pumped through line 57 into line 59 thereby becoming part of the isobutane recycle passed by line 2 into the reaction mixture.

The vapor yield 16' from surge tank 16 is compressed and can optionally be passed through line 24 directly into the isobutane recycle line 30, but preferably is passed into the depropanizer feed through line 26.

The condensed liquid from surge tank 17 is passed through line 18 into the suction of pump 19 from which it is passed through line 22 after being joined by liquid hydrofluoric acid from line 21 in a treating vessel 23 in which the liquid HF separates from the liquid hydrocarbon with the organic fluoride impurities which were in the hydrocarbon now being in the HF to be recycled through line 60 back to the liquid full settler 8 and thence back through the reaction zone where the organic fluoride impurities therein are reacted with isobutane to produce additional alkylate and HF. The hydrocarbon which is predominantly isobutane can be passed directly through line 28 into the isobutane recycle 62 to the reaction feed or, at least in part, can join through line 26 the compressed vapor 16' from surge tank 16 to be fed through preheating heat exchanger 27 and conduit 29 into the depropanizer column 31 to prevent buildup of propane in the alkylation zone. The depropanzing process and HF stripping which complete the processing of the lighter hydrocarbon ends in the process are well known in the art and are set forth here as a typical operation in which propane and HF are taken from the depropanizing column 31 in overhead stream 32, passed through line 34 to be condensed in cooler 35, passed through line 36 into accumulator 37 from which a predominantly HF stream is passed through line 21 back to contactor 23. The hydrocarbon phase containing dissolved HF passed through line 38 into pump 39 as reflux for the depropanizer column with the yield portion charged as feed through line 41 into the HF stripper column 42. From the HF stripper, propane product is taken as a bottoms stream through line 43 and the stripper column overhead comprising HF and propane is returned by line 33 through a condensing step back to the accumulator 37. Bottoms 25 from the depropanizer 31 are used in exchanger 27 indirectly to heat the feed 26 charged to depropanizer 31. The cooled bottoms 30 are recycled through cooler 61 and line 62 to alkylation.

To complete the cycle for the total operation of this process in a typical, preferred operation the liquid from flash tank 47 which by the flashing operation has been enriched in alkylate product is passed through line 66, pump 67, line 68, heat exchanger 69, line 71, heat exchanger 72 and line 74 as the feed into isostripper 75 which is run at high pressure and temperature. From the isostripper, alkylate product containing normal butane can be yielded through line 77. A portion of stream 77 can be passed through fired reboiler 79 and through 81 back to isostripper 75. Another portion of the stream 77 can be passed through line 78 into exchanger 72 indirectly to heat the feed 71 charged through 74 to isostripper 75 and can be removed through line 73.

In the most preferred embodiment of the present invention the hot isobutane vapor taken from the top of the isostripper 75 is passed through line 76 to reboiler 46 of prefractionator 11, to heat exchanger 45 on the prefractionator bottoms outlet, through line 63 and heat exchanger 69 on the isostripper feed line 71, through line 65 with further cooling if necessary to join by way of line 59 the isobutane recycle to the reaction zone. The handling of the alkylate liquid from flash tank 47 to the high pressure and high temperature isostripper does not form a part of the present invention except to complete the integrated process described hereinabove as a preferred operation of the process.

Set out below are calculated values for operating conditions and flows for the typical operation of the system as described above.

| Operating Conditions and Flows | | |
|---|---|---|
| (A) | Operating Conditions: | |
| | HF Alkylation (6): | |
| | Pressure, psia., | 150 |
| | Temperature, °F., | 90 |
| | Total iC$_4$/Olefin Mol Ratio | 13:1 |
| | HF/Total H/C Vol Ratio, | 4:1 |
| | Prefractionator (11): | |
| | Pressure, psia, | 135 |
| | Temperature, °F., | |
| | Top, | 133 |
| | Bottom, | 156 |
| | Flash Zone (14, 15, 16): | |
| | Pressure, psia., | 50 |
| | Temperature, °F., | 70 |
| | Surge (17): | |
| | Pressure, psia., | 120 |
| | Temperature, °F., | 90 |
| | Contactor (23): | |
| | Pressure, psia., | 275 |
| | Temperature, °F., | 90 |
| | Depropanizer (31): | |
| | Pressure, psia., | 265 |
| | Temperature, °F., | |
| | Top, | 122 |
| | Bottom, | 203 |
| | HF Stripper (42): | |
| | Pressure, psia., | 330 |
| | Temperature, °F., | |
| | Top, | 130 |
| | Bottom, | 147 |
| | Flash Tank (47): | |
| | Pressure, psia., | 80 |
| | Temperature °F., | 116 |
| | Accumulator (52): | |
| | Pressure, psia., | 75 |
| | Temperature, °F., | 100 |
| | Isostripper (75): | |

-continued

| Operating Conditions and Flows | | | |
|---|---|---|---|
| | Pressure, psia, | | 250 |
| | Temperature, °F., | | |
| | Top, | | 217 |
| | Bottoms, | | 402 |
| (B) | Flow Rates: (B/D = Barrels/Day) | | |
| (1) | Feed isobutane (iC$_4$) and Olefins B/D, | | 31,362 |
| | Vol. % Olefins, | 38 | |
| | Vol. % iC$_4$, | 48 | |
| | Vol. % Propane, (C$_3$), | 9 | |
| | Vol. % N-Butane, (n-C$_4$), | 5 | |
| (2) | Recycle Isobutane, B/D | | 157,095 |
| | Vol. % iC$_4$ | 89.1 | |
| (9) | Reactor Effluent, B/D | | 186,228 |
| | Vol. % C$_3$, | 3.8 | |
| | Vol. % iC$_4$, | 76.0 | |
| | Vol. % nC$_4$, | 7.2 | |
| | Vol. % isobutane (iC$_5$) Plus | 12.4 | |
| | Vol. % HF, | 0.6 | |
| (12) | Prefractionator Vapor, (equiv.) B/D, | | 29,529 |
| | Vol. % C$_3$, | 10.0 | |
| | Vol. % iC$_4$, | 80.0 | |
| | Vol. % nC$_4$, | 5.9 | |
| | Vol. % iC$_5$ Plus, | 0.3 | |
| | Vol. % HF, | 3.8 | |
| (43) | Propane Yield, B/D, | 3,955 | |
| | Vol. % C$_3$, | 98.5 | |
| | Vol. % iC$_4$, | 1.5 | |
| | Vol. % HF nil (after KOH) | | |
| (21) | HF to Contactor (23), B/D | | 175 |
| (44) | Prefractionator Bottoms, B/D | | 156,699 |
| | Vol. % C$_3$, | 2.7 | |
| | Vol. % iC$_4$, | 75.2 | |
| | Vol. % nC$_4$, | 7.4 | |
| | Vol. % iC$_5$ Plus, | 14.7 | |
| | Vol. % HF, | 0 | |
| (66) | Bottoms to Isostripper (75,) B/D | | 111,753 |
| | Vol. % C$_3$, | 1.8 | |
| | Vol. % iC$_4$ | 70.6 | |
| | Vol. % nC$_4$, | 7.5 | |
| | Vol. % iC$_5$ Plus, | 20.1 | |
| | Vol. % HF, | nil | |
| (76) | Isobutane Vapor from (75), (equivalent) B/D | | 89,049 |
| | Vol. % C$_3$, | 2.3 | |
| | Vol. % iC$_4$, | 88.5 | |
| | Vol. % nC$_4$, | 7.8 | |
| | Vol. % iC$_5$ Plus, | 1.4 | |
| | Vol. % HF, | nil | |
| (25) | Depropanizer Bottoms, B/D | | 41,755 |
| | Vol. % C$_3$, | 1.0 | |
| | Vol. % iC$_4$, | 91.9 | |
| | Vol. % nC$_4$, | 6.6 | |
| | Vol. % iC$_5$ Plus, | 0.5 | |
| | Vol. % HF, | 0 | |
| (48) | Primary Flash Vapor (equivalent), B/D | | 44,946 |
| | Vol. % C$_3$, | 4.9 | |
| | Vol. % iC$_4$, | 86.8 | |
| | Vol. % nC$_4$, | 7.2 | |
| | Vol. % iC$_5$ Plus, | 1.1 | |
| | Vol. % HF, | 0 | |
| (16') | Vapor Yield from 16, (equivalent) B/D | | 17,266 |
| | Vol. % C$_3$, | 7.9 | |
| | Vol. % iC$_4$, | 85.8 | |
| | Vol. % nC$_4$, | 6.0 | |
| | Vol. % iC$_5$ Plus, | 0.3 | |
| | Vol. % HF, | 0 | |
| (40) | Liquid Yield from (16), B/D | | 27,680 |
| | Vol. % C$_3$, | 3.2 | |
| | Vol. % iC$_4$, | 87.3 | |
| | Vol. % nC$_4$, | 7.9 | |
| | Vol. % iC$_5$ Plus, | 1.6 | |
| | Vol. % HF, | 0 | |

I claim:

1. A process for treating the reactor effluent hydrocarbon phase from an alkylation zone in which isoparaffin and olefin are contacted in the presence of HF catalyst to form alkylate product, said method comprising:

(1) separating hydrocarbon phase from the reaction effluent;

(2) separating said hydrocarbon phase in a fractionator to produce a bottoms stream comprising isoparaffin, paraffin, and alkylate product and an overhead stream comprising isoparaffin, paraffin, and HF;

(3) flashing said bottoms stream to produce a flashed vapor enriched in isoparaffin and a liquid enriched in alkylate as compared to said bottoms stream;

(4) cooling said flashed vapor to produce a condensed liquid; and (5) indirectly contactig said overhead stream with said condensed liquid thereby cooling said overhead stream and heating said condensed liquid.

2. A process of claim 1 wherein said condensed liquid is flashed thereby producing a flashed vapor further enriched in paraffin and a liquid further enriched in isoparaffin.

3. A process of claim 2 wherein said flashed vapor further enriched in paraffin is compressed and further treated to remove residual isoparaffin.

4. A method of claim 1 or 3 wherein said overhead stream is
 (a) condensed;
 (b) pumped to contact with HF thereby removing organic fluoride; and
 (c) subjected to treatment effecting separation of paraffin from isoparaffin.

5. A method of claim 2 wherein said liquid further enriched in isoparaffin is recycled to said alkylation zone.

6. A method of claim 4 wherein said liquid further enriched in isoparaffin is recycled to said alkylation zone.